US006903354B2

(12) United States Patent
Goldstein

(10) Patent No.: US 6,903,354 B2
(45) Date of Patent: Jun. 7, 2005

(54) EXTREME ULTRAVIOLET TRANSITION OSCILLATOR

(75) Inventor: Michael Goldstein, Ridgefiled, CT (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 10/371,541

(22) Filed: Feb. 21, 2003

(65) Prior Publication Data

US 2004/0183486 A1 Sep. 23, 2004

(51) Int. Cl.[7] .................................................. A61N 5/00

(52) U.S. Cl. ................................ 250/492.3; 250/492.2; 315/111.81

(58) Field of Search ........................... 250/492.3, 492.2, 250/492.21, 492.1, 365, 372; 315/149, 150, 111.81

(56) References Cited

U.S. PATENT DOCUMENTS

| | | | | | |
|---|---|---|---|---|---|
| 4,763,344 | A | | 8/1988 | Piestrup | 378/119 |
| 5,045,695 | A | * | 9/1991 | Rule et al. | 250/305 |
| 5,914,492 | A | * | 6/1999 | Wang et al. | 250/397 |
| 6,410,928 | B1 | * | 6/2002 | Verhoeven et al. | 250/492.2 |

OTHER PUBLICATIONS

A.N. Chu, M.A. Piestrup, T.E. Barbee Jr., and R.H. Pantell, "Transition radiation as a source of X–Rays", J. Appl. Phys. 51(3), Mar. 1980.

M.A. Pierstrup, "Measurement of transition radiation from medium–energy electrons", Phys. Rev. A, 32(2), Aug. 1985.

M.J. Moran, B.A. Dahling, P.J. Ebert, et al. "Measurement of Coherent Transition X Rays", Phys. Rev. Lett. 57(10), Sep. 8, 1996.

W. Knulst, .J. Luiten, M.J. van der Wiel, "A Tabletop Soft X–Ray Source based on 5–10 meV Linacs", Proceedings of EPAC 2000, Vienna, Austria.

W. Knulst, O.J. Luiten, and M.J. van der Wiel, "Observation of narrow–band Si L–edge Cerenkov radiation generated by 5 MeV electrons", Appl. Phys. Lett., 79(18), Oct. 29, 2001.

M.A. Piestrup, P.F. Finman, "The Prospects of an X–Ray Free Electron Laser Using Stimulated Resonance Transition Radiation", IEEE J. Quantum Electron, 19(3), Mar. 1983.

G. Bekefi, J.S. Wurtele, J.H. Deutsch, "Free–electron–laser radiation induced by a periodic dielectric medium", Phys. Rev. A, 34(2), Aug. 1986.

M.B. Reid, M.A. Piestrup, "Resonance Transition Radiation X–Ray Laser", IEEE J. Quantum Electron, 27(11), Nov. 1991.

V.V. Apollonov, A.L. Artemyev, M.V. Fedorov, et al., "Free–electron laser exploiting a superlattice–like medium", Optics Expr., 3(5), Jul. 20, 1998.

R.A. Crowell, C.D. Jonah, A.D. Trifunac, J. Qian, "Laser System for a subpicosecond Electron LINAC", Chemistry Division, Argonne National Laboratory, contract No. W–31–109–ENG–38 (http://epaper.kek.jp/198/PAPERS/Mo4025.PDF).

(Continued)

*Primary Examiner*—Tuyet Thi Vo
(74) *Attorney, Agent, or Firm*—Fish & Richardson P.C.

(57) ABSTRACT

Systems and techniques to generate extreme ultraviolet (EUV) illumination. An EUV system includes first layers, and second layers interleaved with the first layers, where the first layers and the second layers have a thickness selected to produce coherent transition radiation in an extreme ultraviolet wavelength region when an electron beam passes through the first layers and the second layers. The first and second layers may be built using thin film deposition techniques and etching techniques. The first layers may include metal, such as molybdenum. The second layers may include a dielectric material and may define regions of vacuum between the first layers, including possibly multiple regions of vacuum per layer.

37 Claims, 3 Drawing Sheets

OTHER PUBLICATIONS

F.B. Kiewiet, "Generation of ultra–short, high–brightness relativistic electron bunches", Ph.D. Thesis, Technische Universiteit Eindhoven, 2003.

L.R. Elias, "High–Power, cw, Tunable (uv through ir) Free–Electron Laser Using Low–Energy Electron Beams", Phys. Rev. Lett., 42(15), pp. 977, Apr. 9, 1979.

J.D. Jackson, "Classical Electrodynamics", (John Wile & Sons, NY, 1975), $2^{nd}$ Ed., p. 685–693.

K.A. Goldbert, P. Naulleau, S. Rekawa, et al., "At–Wavelength Interferometry of High–NA Diffraction–Limited EUV Optics", Preprint,.$8^{th}$ Int. Conf. on Synch. Rad. Instrumentation, Aug. 28, 2003.

J. Gea–Banaclocke, G.T. Moore, R.R. Schlicher, et al., "Soft X–Ray Free–Electron Laser with a Laser Undulator", IEEE Journal of Quantum Electronics, vol. QE–23, No. 9, Sep. (1987).

S. Humphries, "Charged Particle Beams" (Table of Contents), New York: John Wiley & Wons, Inc. 1990.

L.H. Yu et al., "High–Gain Harmonic–Generation Free–Electron Laser," Science Mag. vol. 289, Aug. 11, 2000.

Juhao Wu et al., "Coherent hard X–ray production by cascading stages of High Gain Harmonic Generation", Elsevier Science B.V., 2001 p. 014–111.

N.N. Nasonov et al., "X rays from relativistic electrons in a multilayer structure", The America Physical Society, 2003.

Danny Y. Wang et al., "Gain and Efficiency of a Stimulated Cherenkov Optical Klystron", IEEE, vol. QE–'9, No. 3, Mar. 1983.

C.K. Chen et al., "Analysis of bunching of an electron beam at optical wavelengths", J. Appl. Phys. 49(1), Jan. 1978.

M. J. Moran et al., "Measurement of x–ray dielectric constants with coherent transition radiation", 146/SPIE vol. 690 X Rays in Materials Analysis: Novel Applications and Recent Developments (1986).

M.J. Moran et al., "Transition Radiation as a Coherent Soft X–ray Source", American Institute of Physics, 1986.

G. Case, et al., "Measurements of Compton Scattered Transition Radiation at High Lorentz Factors," Jan. 9, 2003, arXiv:hep–ex/0209038 v1.

X. Artru, et al., "Practical theory of the multilayered transition radiation detector," Apr. 7, 1975, Physical Review D, vol. 12, No. 5.

M. Cherry, et al., "The Efficient Identification of Relativistic Particles by Transition Radiation," Aug. 21, 1973, Nuclear Instruments & Methods, vol. 115, No. 1.

L. Yuan, et al., "Energy Dependence of X–Ray Transition Radiation From Ultrarelativistic Charged Particles," Mar. 16, 1970, Physics Letters, vol. 31B, 1970.

* cited by examiner

EXTREME ULTRAVIOLET TRANSITION OSCILLATOR

BACKGROUND

The present application describes systems and techniques relating to extreme ultraviolet light sources, for example, extreme ultraviolet light sources used in extreme ultraviolet light lithography or interferometry.

Traditionally recognized extreme ultraviolet (EUV) light sources include synchrotrons and plasma-based sources. A synchrotron is an annular particle accelerator that can produce synchrotron radiation or a free electron laser using wiggler magnets. Synchrotrons are generally large and expensive high energy devices, which may be able to radiate in the EUV region.

Plasma-based sources of EUV light include electric discharge plasma sources and laser discharge plasma sources. Typically, a jet of xenon gas is excited into a plasma using a laser or electricity. The plasma then provides atomic spectral radiation in the EUV range. Plasma-based EUV sources generate high energy ions, which tend to sputter any materials that fall in a line of sight of the plasma. Additionally, plasma-based EUV sources tend to have low energy efficiency and use extensive cooling systems.

DRAWING DESCRIPTIONS

Details of one or more embodiments are set forth in the accompanying drawings and the description below. Other features and advantages may be apparent from the description and drawings, and from the claims.

DETAILED DESCRIPTION

The systems and techniques described here relate to extreme ultraviolet (EUV) light sources. A transition oscillator may be built using thin film deposition techniques such that, when a mildly relativistic electron beam passes through the transition oscillator, a coherent superposition of transition radiation is produced at EUV wavelengths. Thus, the transition oscillator may be used as a compact, high brightness, EUV illumination source in various EUV applications, such as EUV lithography and EUV interferometry. The EUV illumination source may be built into a portable device that may be used easily at various locations, such as a compact interferometer that may be used to test a set of optics on-site or with an EUV lithography tool that may ship from an exposure tool supplier to a semiconductor manufacturing facility. The EUV illumination source may provide high brightness EUV radiation with high stability, low cost of ownership, and without debris formation.

Figure 1:
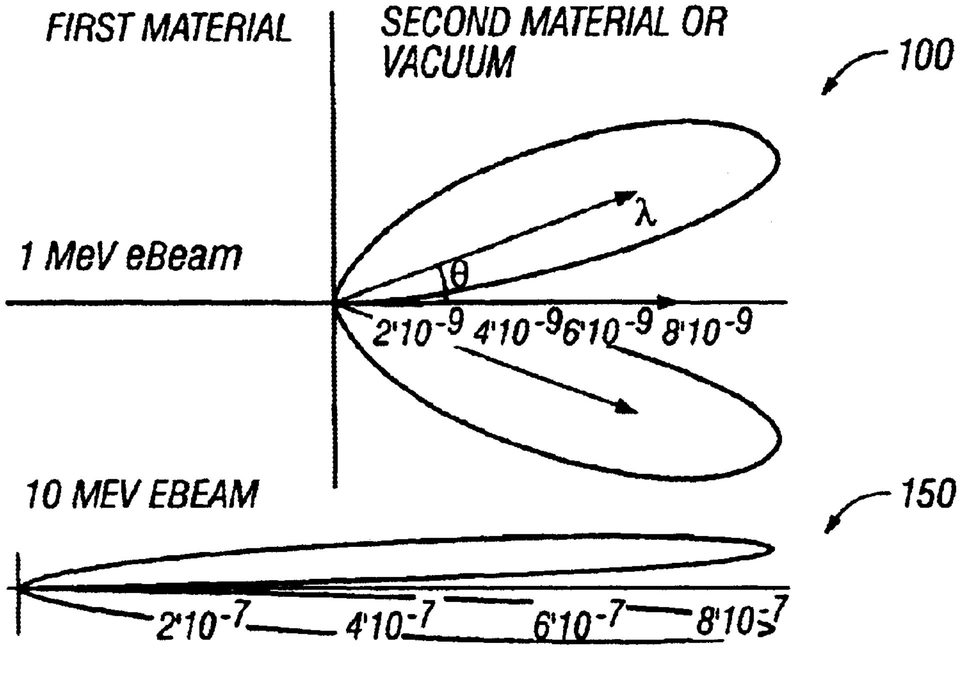
FIG. 1 illustrates transition radiation.

FIG. 1 illustrates transition radiation. When a mildly relativistic beam of electrons (e.g., 1 MeV or more) crosses the interface between two mediums with different dielectric or magnetic properties, forward directed radiation is created that is called transition radiation. This transition radiation becomes more forwardly directed as the electron beam becomes more relativistic. As the energy level of the electron beam increases, the energy of the transition radiation concentrates to a smaller solid angle.

A graph 100 illustrates transition radiation generated when a 1 MeV electron beam passes from a first material into a second material or vacuum. The peak intensity generally occurs at an angle of 18.4 degrees from the direction of the electron beam direction. A graph 150 illustrates transition radiation generated when a 10 MeV electron beam passes from a first material into a second material or vacuum. The peak intensity at this e-beam energy generally occurs at an angle of 2.78 degrees from the direction of the electron beam direction.

Figure 2:
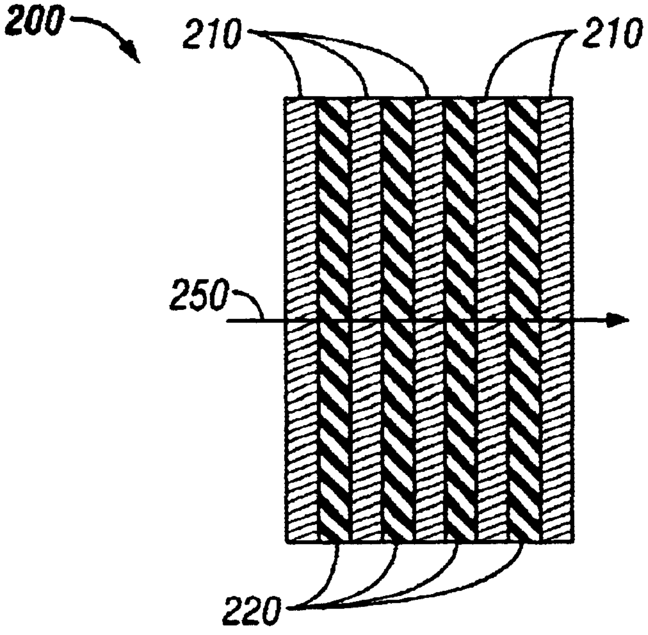
FIG. 2 illustrates an example extreme ultraviolet transition oscillator.

FIG. 2 illustrates an example extreme ultraviolet transition oscillator 200. The EUV transition oscillator 200 may be part of an apparatus used to generate extreme ultraviolet light by producing coherent transition radiation. The EUV transition oscillator 200 may include multiple metal layers 210 interleaved with multiple dielectric layers 220. The metal and dielectric layers 210, 220 have a thickness selected to produce coherent transition radiation in an extreme ultraviolet wavelength region when an electron beam 250 passes through the metal layers 210 and the dielectric layers 220. The thickness is selected based on the desired wavelength of the coherent transition radiation, such as a per-layer optical thickness of 13 nm.

The layers 210, 220 may be deposited on a substrate using thin film deposition techniques. A first layer of the thin films deposited on the substrate may be exposed, such as by back-etching, to create a free-standing multi-layer stack, which may then be placed in the path of an electron beam. The substrate may be a silicon wafer, and the manufacturing process may also provide a supporting frame for the multi-layer stack. The metal layers may be thin films of molybdenum. The dielectric layers may be thin films of silicon.

The metal layers may have a per-layer thickness of between 5 and 50 nanometers, and the dielectric layers may also have a per-layer thickness of between 5 and 50 nanometers. The per-layer thickness may be selected based on a desired wavelength for the transition radiation and the materials being used. The metal layers may be selected to have a per-layer thickness of one wavelength, which causes the transition radiation off the front and back surfaces of a metal layer to add up coherently (i.e., constructive interference). A one wavelength separation from the back surface of one metal layer to the front surface of the next metal layer may also be used. Other non-regular thicknesses may be used to shape the power spectra, to reduce sensitivities to manufacturing/heating tolerances, and to optimize power output in absorbing materials.

By using thin film deposition techniques to produce the metal and dielectric layers, precise control over the thickness of the layers and the spacing of the layers is provided. Thin film deposition techniques are used widely in the semiconductor industry, such as the thin film deposition techniques used to create Bragg reflectors, and are an efficient and cost effective way to produce transition oscillators as described herein.

Figure 3:
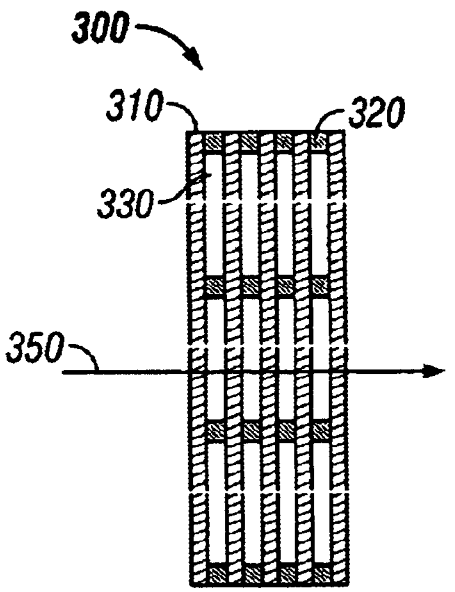
FIG. 3 illustrates another example extreme ultraviolet transition oscillator.

FIG. 3 illustrates another example extreme ultraviolet transition oscillator 300. The EUV transition oscillator 300 may be part of an EUV illumination apparatus, just as the EUV transition oscillator 200 from FIG. 2, and may be built in a similar manner. The EUV transition oscillator 300 may include multiple interleaved metal layers 310 and dielectric layers 320, which have a thickness selected to produce coherent transition radiation in an extreme ultraviolet wavelength region when an electron beam 350 passes through the layers.

The dielectric layers 320 act as spacers that define regions of vacuum 330 between the metal layers 310 in areas between the spacers. The dielectric layers may define multiple regions of vacuum per layer, as shown. This structure may provide a constant separation between the metal layers and additional strength and stability. Alternatively, the metal layers of the EUV transition oscillator 300 may be held together on the edges alone, such as by a supporting frame built around the transition oscillator 300.

As before, the layers 310, 320 may be deposited on a substrate using thin film deposition techniques. This depositing may involve applying layer patterns lithographically. The dielectric layers may be hollowed out using etching techniques to create the regions of vacuum. For example, the dielectric layers may include a material having properties of etch selectivity and thermal stability, such as silicon carbide. A series of holes may be drilled through the multi-layer thin film stack (e.g., a contact array may be etched through the stack), and then the dielectric material may be etched out from between the metal layers using an etch process that is selective for one material over the other.

A first layer of the thin films deposited on the substrate may be exposed to create a free-standing multi-layer metal-vacuum stack, which may then be placed in the path of an electron beam. The electron beam may be one millimeter in diameter. Thus in some implementations, the electron beam would still pass through some of the dielectric material left in the dielectric layers to provide stability to the EUV transition oscillator 300. The hollowed out dielectric layers may have widths that are larger than the metal layers, such as a per-layer thickness of two wavelengths.

These multi-layer metal-dielectric and metal-vacuum transition oscillators may be included in an apparatus or system that passes a mildly relativistic electron beam through the multi-layer stack. The multi-layer structure provides a high degree of control over the relative phase of transition radiation from successive interfaces so that coherent superposition at a design wavelength is achieved.

Increasing the number of total layers, or periods, in the multi-layer structure increases the power and intensity of the resulting transition radiation, but with generally diminishing returns. The transition oscillators 200, 300 may have approximately one hundred periods, such as at least forty-five metal layers and at least forty-five dielectric/vacuum layers, which results in about a fifty percent transmission. Additional layers increase absorption of the transition radiation generated by the previous layers. Thus, there is likely an upper bound for radiated power of the structure based on the thermal limits of the materials being used.

Power in the range of tens of Watts may be generated. Using an approximately one millimeter electron beam diameter, a high brightness [Watts/(cm^2 area×nm bandwidth×strRad] EUV light source may be created.

Figure 4:
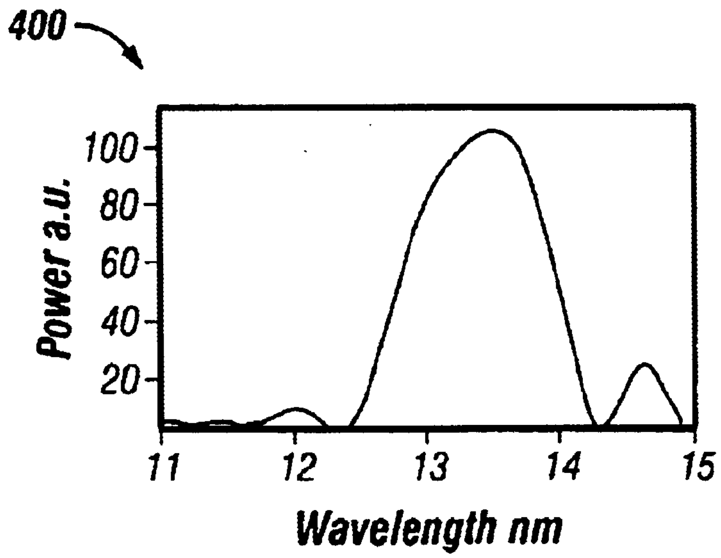
FIG. 4 illustrates an approximated power spectra of an extreme ultraviolet transition oscillator.

FIG. 4 illustrates an approximated power spectra of an extreme ultraviolet transition oscillator. A graph 400 shows power graphed against wavelength. Additional conclusions regarding the potential power of an apparatus using these systems and techniques may be obtained by additional analysis of the spectra, efficiency and thermal limits involved.

Figure 5:
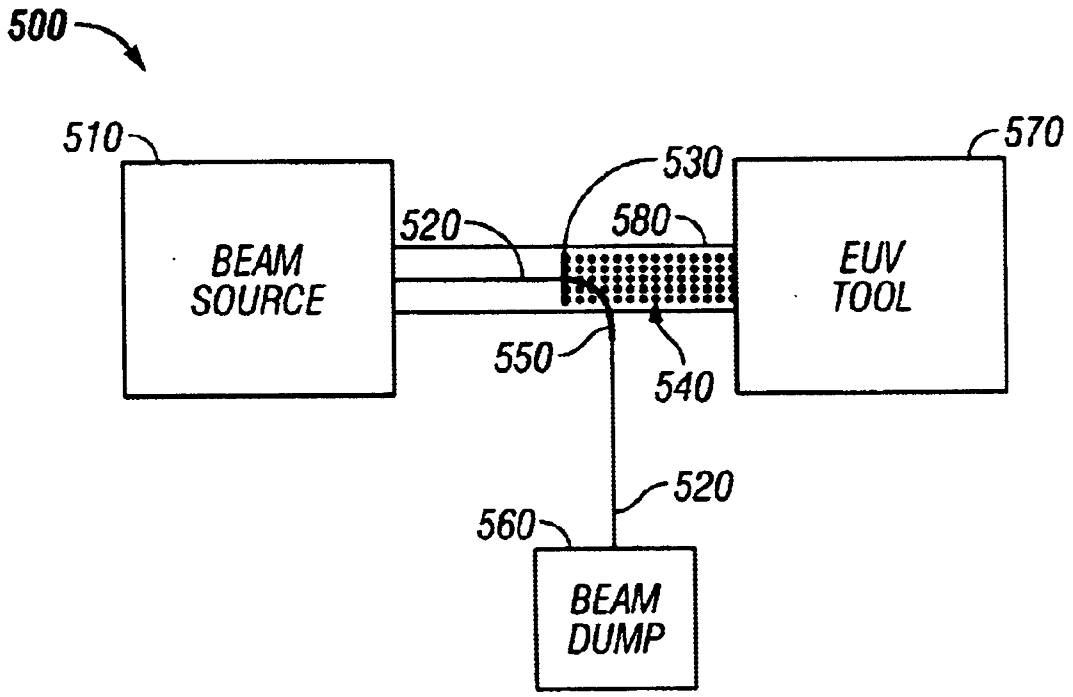
FIG. 5 illustrates an extreme ultraviolet light system.

FIG. 5 illustrates an extreme ultraviolet light system 500. The system 500 includes a beam source 510. The beam source 510 may be a compact linear accelerator (e.g., a 10 MeV electron pump source), such as a Varian 10 MeV Linac provided by Varian Associates Corporation of Palo Alto, Calif. The system 500 includes a vacuum chamber 580 and a transition oscillator 530, such as described above. The vacuum chamber 580 can be an ultra-high vacuum tube system with the multi-layer stack suspended inside. The system 500 also includes a beam diverter 550 and a beam dump 560.

The beam source 510 generates a relativistic electron beam 520, such as a beam of 10 MeV electrons with a focal spot size of one millimeter. The electron beam 520 passes through the multi-layer stack, which generates EUV illumination 540. The metal layers of the multi-layer stack may have an electron plasma frequency near 20 eV, and the multi-layer stack may radiate in the extreme ultraviolet wavelength region at about 13.5 nm. The beam 520 then passes through, and is redirected by, the beam diverter 550 (e.g., a bending magnet) to fall on the beam dump 560.

The beam dumb 560 may be configured as Faraday cup and may also electromagnetically slow the beam to recapture energy prior to absorbing the current. The beam dumb may be constructed with using a combination of Carbon and metals or other materials. Active cooling may be required.

The total thickness of the multi-layer stack is substantially smaller than the electron mean free path so very little energy from the electron beam 520 is deposited in the multi-layer stack by way of scattering. The illumination 540 is created at the transition oscillator 530 and provided to an exit aperture. Almost all of the unwanted energy is in the form of the beam 520, which can be dumped far away from the transition oscillator 530. Thus, the heating issues for the system 500 are generally limited to heating caused by the partial absorption of the transition radiation by the transition oscillator 530.

The system 500 may also include an EUV tool 570. The EUV tool 570 may include various components that are reflective and coated with distributed quarter-wave Bragg reflectors. The illumination 540 may be provided to the EUV tool 570 for various purposes, such as for lithography or actinic interferometric measurement of EUV mirrors.

The EUV tool 570 may be an EUV interferometer or an EUV lithography tool. The EUV interferometer may be a tool for testing optical systems. The EUV lithography tool may be an integrated circuit (IC) manufacturing system used to transfer circuit patterns from a mask to a silicon substrate.

The IC manufacturing system may include a low-expansion reflective reticle attached to a scanning reticle stage that moves the mask across the EUV illumination, which may be redirected with optics. The IC manufacturing system may also include a scanning wafer stage, which holds a semiconductor wafer coated with EUV-sensitive photoresist, that synchronously scans the wafer across the reflected EUV illumination with nanometer precision. The two scanning stages may be magnetically levitated. The IC manufacturing system may also include a reflective optical system with aspheric components to produce a reduction of the mask image that illuminates the wafer.

Figure 6:
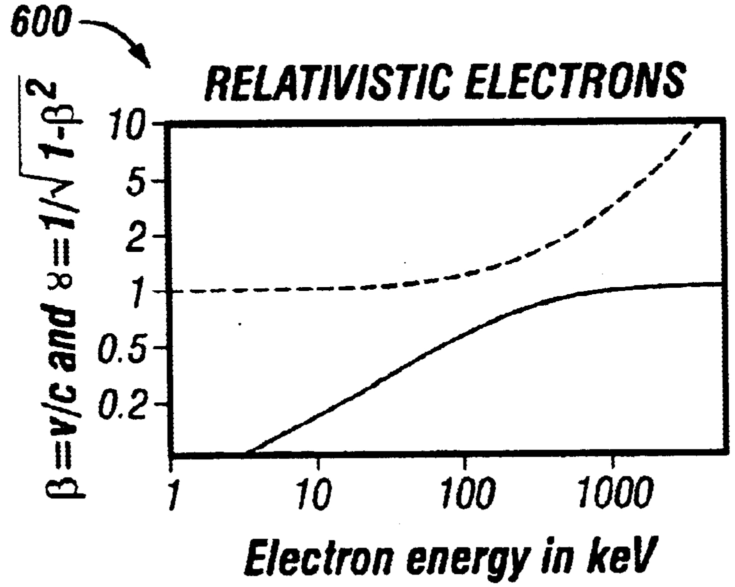
FIG. 6 illustrates a calculated relativistic factor for an electron beam used in the system of FIG. 5.

FIG. 6 illustrates a calculated relativistic factor for an electron beam used in the system of FIG. 5. A graph 600 shows $\beta \equiv v/c$ and $\gamma \equiv 1/\sqrt{1-\beta^2}$ by electron energy in KeV.

The various implementations described above have been presented by way of example only, and not limitation. Other embodiments may be within the scope of the following claims.

What is claimed is:

1. An apparatus comprising:

a plurality of metal layers; and a plurality of dielectric layers interleaved with the plurality of metal layers, wherein the plurality of metal layers and the plurality of dielectric layers have a thickness selected to produce coherent transition radiation in an extreme ultraviolet wavelength region when an electron beam passes through the plurality of metal layers and the plurality of dielectric layers;

wherein the plurality of dielectric layers define regions of space between the plurality of metal layers.

2. The apparatus of claim 1, wherein the plurality of metal layers have a per-layer thickness of between 5 and 50 nanometers, and the plurality of dielectric layers have a per-layer thickness of between 5 and 50 nanometers.

3. The apparatus of claim 1, wherein the plurality of metal layers comprise molybdenum.

4. The apparatus of claim 1, wherein the plurality of dielectric layers comprise silicon.

5. The apparatus of claim 1, wherein the plurality of dielectric layers define multiple regions of space per layer.

6. The apparatus of claim 1, wherein the plurality of metal layers comprise at least forty-five metal layers, and the plurality of dielectric layers comprise at least forty-five dielectric layers.

7. The apparatus of claim 1, wherein the plurality of dielectric layers comprise a material having properties of etch selectivity and thermal stability.

8. The apparatus of claim 7, wherein the plurality of dielectric layers comprise silicon carbide.

9. A method comprising:

depositing a plurality of thin films on a substrate, the thin films comprising a plurality of dielectric layers and a plurality of metal layers interleaved with the plurality of dielectric layers, wherein the plurality of metal layers and the plurality of dielectric layers have a thickness to produce coherent transition radiation in an extreme ultraviolet wavelength region when an electron beam passes through the plurality of metal layers and the plurality of dielectric layers; and exposing a first layer of the plurality of thin films deposited on the substrate;

wherein the method further comprises hollowing out the plurality of dielectric layers.

10. The method of claim 9, further comprising passing a relativistic electron beam through the plurality of thin films.

11. The method of claim 10, wherein the relativistic electron beam has an energy level of about 10 MeV.

12. The method of claim 9, wherein said exposing comprises back-etching the substrate.

13. The method of claim 9, wherein said depositing comprises depositing a material having properties of etch selectivity and thermal stability.

14. The method of claim 9, wherein said depositing comprises depositing the plurality of metal layers with a per-layer thickness of between 5 and 50 nanometers, and depositing the plurality of dielectric layers with a per-layer thickness of between 5 and 50 nanometers.

15. The method of claim 9, wherein said depositing comprises depositing the plurality of dielectric layers comprising at least forty-five layers and depositing the plurality of metal layers comprising at least forty-five layers.

16. A system comprising:

a beam source providing an electron beam;

a vacuum chamber coupled with the beam source;

a transition oscillator in the vacuum chamber, the transition oscillator comprising a multi-layer thin-film stack having a per-layer thickness selected to produce coherent transition radiation in an extreme ultraviolet wavelength region when the electron beam passes through the multi-layer thin-film stack; and an extreme ultraviolet interferometer coupled with the vacuum chamber;

wherein the multi-layer thin film stack comprises at least one first layer defining at least one region of space between additional layers of the multi-layer thin film stack.

17. The system of claim 16, wherein the multi-layer thin-film stack comprises at least ninety layers.

18. The system of claim 16, wherein the extreme ultraviolet interferometer comprises an optics test bench.

19. The system of claim 16, wherein the at least one first layer defines multiple regions of space between the additional layers.

20. The system of claim 19, wherein the multi-layer thin film stack comprises a metal-dielectric stack comprising a plurality of dielectric layers, including the at least one first layer, that define multiple regions of space per dielectric layer.

21. A system comprising:

a beam source providing an electron beam;

a vacuum chamber coupled with the beam source;

a transition oscillator in the vacuum chamber, the transition oscillator comprising a multi-layer thin-film stack having a per-layer thickness selected to produce coherent transition radiation in an extreme ultraviolet wavelength region when the electron beam passes through the multi-layer thin-film stack;

an extreme ultraviolet interferometer coupled with the vacuum chamber;

a beam diverter; and a beam dump.

22. The system of claim 21, wherein the multi-layer thin-film stack comprises a metal-dielectric stack.

23. The system of claim 21, wherein the multi-layer thin-film stack comprises a metal-vacuum stack.

24. A system comprising:

a beam source providing an electron beam;

a vacuum chamber coupled with the beam source;

a transition oscillator in the vacuum chamber, the transition oscillator comprising a multi-layer thin-film stack having a per-layer thickness selected to produce coherent transition radiation in an extreme ultraviolet wavelength region when the electron beam passes through the multi-layer thin-film stack; and an extreme ultraviolet lithography system coupled with the vacuum chamber;

wherein the multi-layer thin film stack comprises at least one first layer defining at least one region of space between additional layers of the multi-layer thin film stack.

25. The system of claim 24, wherein the multi-layer thin-film stack comprises at least ninety layers.

26. The system of claim 24, wherein the extreme ultraviolet lithography system comprises an integrated circuit manufacturing system.

27. The system of claim 24, wherein the at least one first layer defines multiple regions of space between the additional layers.

28. The system of claim 27, wherein the multi-layer thin film stack comprises a metal-dielectric stack comprising a plurality of dielectric layers, including the at least one first layer, that define multiple regions of space per dielectric layer.

29. A system comprising:

a beam source providing an electron beam;

a vacuum chamber coupled with the beam source;

a transition oscillator in the vacuum chamber, the transition oscillator comprising a multi-layer thin-film stack having a per-layer thickness selected to produce coherent transition radiation in an extreme ultraviolet wavelength region when the electron beam passes through the multi-layer thin-film stack;

an extreme ultraviolet lithography system coupled with the vacuum chamber;

a beam diverter; and a beam dump.

30. The system of claim 29, wherein the multi-layer thin-film stack comprises a metal-dielectric stack.

31. The system of claim 29, wherein the multi-layer thin-film stack comprises a metal-vacuum stack.

32. An apparatus comprising:

a plurality of first layers comprising metal; and a plurality of second layers interleaved with the plurality of first layers, wherein the plurality of first layers and the plurality of second layers have a thickness selected to produce coherent transition radiation in an extreme ultraviolet wavelength region when an electron beam passes through the plurality of first layers and the plurality of second layers, and wherein the plurality of second layers define regions of space between the plurality of first layers.

33. The apparatus of claim 32, wherein the plurality of second layers comprise a dielectric material.

34. The apparatus of claim 32, wherein the plurality of second layers define multiple regions of space per layer.

35. The apparatus of claim 32, wherein the plurality of second layers comprise a material having properties of etch selectivity and thermal stability.

36. The apparatus of claim 35, wherein the material comprises silicon carbide.

37. The apparatus of claim 32, wherein the plurality of first layers comprise at least forty-five first layers, and the plurality of second layers comprise at least forty-five second layers.

* * * * *